United States Patent [19]

Farooq et al.

[11] Patent Number: 4,699,913
[45] Date of Patent: Oct. 13, 1987

[54] SUBSTITUTED 4,5-DIHYDRO-1,3,4-THIADIAZOLES USEFUL AS INSECTICIDES

[75] Inventors: Saleem Farooq, Arisdorf; Josef Ehrenfreund; Hans-Rudolf Waespe, both of Allschwil, all of Switzerland

[73] Assignee: Ciba-Geigy Corporation, Ardsley, N.Y.

[21] Appl. No.: 876,035

[22] Filed: Jun. 19, 1986

[30] Foreign Application Priority Data

Jun. 28, 1985 [CH] Switzerland ............... 2752/85
Aug. 23, 1985 [CH] Switzerland ............... 3640/85
May 27, 1986 [CH] Switzerland ............... 2131/86

[51] Int. Cl.$^4$ .................. C07D 417/04; A61K 31/44
[52] U.S. Cl. .................. 514/333; 514/342; 546/256; 546/277; 546/332
[58] Field of Search ............ 546/256, 277; 514/333, 514/342

[56] References Cited

PUBLICATIONS

Chem. Abstract 4287b, vol. 60 (1964) of British Pat. No. 900,815, Jul. 1962.
Zelenin et al., English Translation of Khim. Geterotsikl. Soldin (No. 7), pp. 683–689 (1982).
Evans et al., J. Chem. Soc., Chem. Commun. 1982, pp. 188–189.

*Primary Examiner*—John M. Ford
*Assistant Examiner*—Bernard I. Dentz
*Attorney, Agent, or Firm*—Edward McC. Roberts; Kevin T. Mansfield

[57] ABSTRACT

The invention relates to novel unsubstituted or substituted 2-phenyl-5-pyridyl-4,5-dihydro-1,3,4-thiadiazoles of the formula

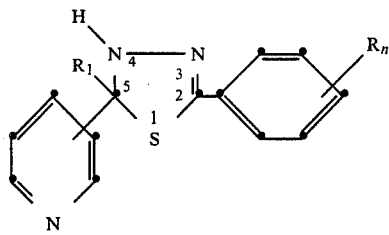

wherein
$R_1$ is hydrogen or $C_1$–$C_4$alkyl;
R is hydrogen, $C_1$–$C_4$alkyl, halogen, nitro, cyano, $C_1$–$C_4$alkoxy, $C_1$–$C_4$alkylthio, $C_1$–$C_4$haloalkyl containing 1 to 9 halogen atoms, $C_1$–$C_4$haloalkoxy containing 1 to 9 halogen atoms, $C_1$–$C_4$haloalkylthio containing 1 to 9 halogen atoms, phenyl, substituted phenyl, phenylalkyl, substituted phenylalkyl, phenoxy, substituted phenoxy, phenylthio, substituted phenylthio, pyridyloxy or substituted pyridyloxy and
n is a value from 1 to 5;
and to the salts and optical isomers thereof; to the preparation of these compounds and to compositions containing them for use in pest control, in particular for controlling insects that attack plants and animals. The novel compounds exhibit in particular good activity against plant-destructive sucking insects.

16 Claims, No Drawings

SUBSTITUTED 4,5-DIHYDRO-1,3,4-THIADIAZOLES USEFUL AS INSECTICIDES

The present invention relates to novel unsubstituted or substituted 2-phenyl-5-pyridyl-4,5-dihydro-1,3,4-thiadiazoles, to the preparation thereof and to the use thereof in pest control.

The present invention relates to novel compounds of formula I

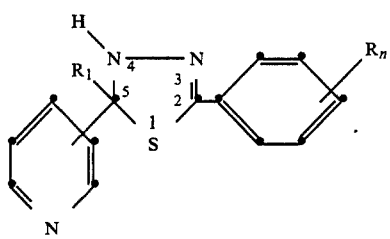

wherein $R_1$ is hydrogen or $C_1$-$C_4$alkyl;

R is hydrogen, $C_1$-$C_4$alkyl, halogen, nitro, cyano, $C_1$-$C_4$alkoxy, $C_1$-$C_4$alkylthio, $C_1$-$C_4$haloalkyl containing 1 to 9 halogen atoms, $C_1$-$C_4$haloalkoxy containing 1 to 9 halogen atoms, $C_1$-$C_4$haloalkylthio containing 1 to 9 halogen atoms, phenyl, substituted phenyl, phenylalkyl, substituted phenylalkyl, phenoxy, substituted phenoxy, phenylthio, substituted phenylthio, pyridyloxy or substituted pyridyloxy and n is a value from 1 to 5;

and to the salts and optical isomers thereof.

Preferred compounds of formula I are those wherein $R_1$ is hydrogen or $C_1$-$C_4$alkyl;

R is hydrogen, $C_1$-$C_4$alkyl, halogen, nitro, cyano, $C_1$-$C_4$alkoxy, $C_1$-$C_4$alkylthio, $C_1$-$C_4$haloalkyl containing 1 to 9 halogen atoms, $C_1$-$C_4$haloalkoxy containing 1 to 9 halogen atoms or $C_1$-$C_4$haloalkylthio containing 1 to 9 halogen atoms and n is a value from 1 to 5.

Further preferred compounds of formula I are those wherein n is 1 or 2.

If R in the compounds of formula I is substituted phenyl, substituted phenylalkyl, substituted phenoxy, substituted phenylthio or substituted pyridyloxy, which radicals may be substituted by one to three substituents, preferably one substituent, then possible substituents are, independently, preferably the following: $C_1$-$C_4$alkyl, halogen, preferably fluorine or chlorine, nitro, cyano, $C_1$-$C_4$alkoxy, $C_1$-$C_4$alkylthio, $C_1$-$C_4$haloalkyl containing 1 to 9 halogen atoms, $C_1$-$C_4$haloalkoxy containing 1 to 9 halogen atoms and $C_1$-$C_4$haloalkylthio containing 1 to 9 halogen atoms.

Of particular interest are those compounds of formula Ia

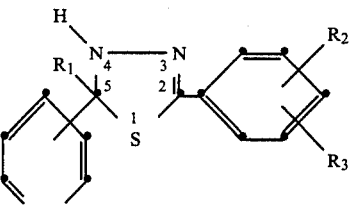

wherein $R_1$ is hydrogen or $C_1$-$C_4$alkyl;

$R_2$ and $R_3$ are each independently of the other hydrogen, halogen, $C_1$-$C_4$alkyl, trifluoromethyl, $C_1$-$C_4$alkoxy or nitro;

as well as the salts thereof, and, in particular, those compounds of formula Ia, wherein $R_1$ is hydrogen, methyl or ethyl;

$R_2$ and $R_3$ are each independently of the other hydrogen or halogen which is in the 2- and/or 4-position.

In addition, preferred compounds of formulae I and Ia are those wherein $R_1$ and/or $R_3$ are hydrogen.

Those compounds of formulae I and Ia wherein the pyridyl group is attached in its 3-position to the 4,5-dihydro-1,3,4-thiadiazole ring in the 5-position are particularly interesting on account of their biological activity.

The present invention also relates to the salts, in particular the phytophysiologically acceptable salts, of the compounds of formulae I and Ia. Such salts with organic and inorganic acids are e.g. the following: chlorides, bromides, iodides, sulfates, hydrogen sulfates, chlorates, perchlorates, rhodanides, nitrates, phosphates, hydrogen phosphates, tetrafluoroborates, formiates, acetates, trichloroacetates, trifluoroacetates, phenylsulfonates, oxalates, malonates, succinates, malates, tartrates or citrates.

The present invention also relates to the optical isomers of the compounds of formulae I and Ia which can be obtained from the racemic forms in a manner known per se by conventional separation methods.

The compounds of formulae I and Ia can be prepared in a manner known per se (q.v. D. M. Evans et al., J. Chem. Soc., Chem. Commun. 1982, p. 188; K. N. Zelenin et al., Khim. Geterotsikl. Soedin, 1982 (No. 7), p. 904) by reacting a compound of formula II

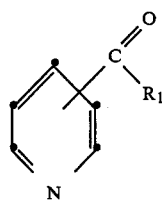

with a compound of formula III

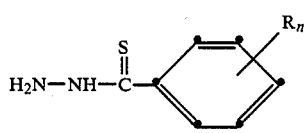

in which compounds of formulae II and III $R_1$, R and n are as defined above for formula I [process (a)].

The compounds of formulae I and Ia can also be prepared in novel manner by reacting a compound of formula IV

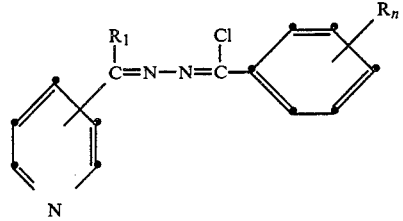

wherein $R_1$, R and n are as defined above for formula I, with a sulfide [process (b)].

If desired, a compound of formula I or Ia obtained as described above can be converted in a manner known per se to a salt thereof.

Process (a) yielding compounds of formulae I and Ia is preferably carried out in a solvent. Suitable solvents are e.g. aromatic hydrocarbons such as benzene, toluene and xylene; ketones such as acetone, cyclohexanone and methyl ethyl ketone; ethers such as tetrahydrofuran, dioxane and diethyl ether; halogenated hydrocarbons such as chloroform, carbon tetrachloride and chlorobenzene; alcohols such as ethanol and propanol; esters of aliphatic acids such as ethyl acetate; aliphatic amides such as dimethylformamide and dimethylacetamide; dimethyl sulfoxide and other solvents which do not impair the reaction. The solvents may also be employed as mixtures. The reaction temperatures may be in a wide range from $-10°$ to $+200°$ C. A temperature range from room temperature to about 150° C. is preferred.

Process (b) is preferably carried out in a polar solvent such as water, or an alcohol, e.g. methanol or ethanol. The cyclisation is effected with a sulfide, preferably a soluble metal sulfide such as sodium sulfide or potassium sulfide, or a corresponding hydrogen sulfide, with an alkaline medium being preferred. The reaction temperature may be in the range from $-15°$ to $+100°$ C. A temperature in the range from $-10°$ C. to $+50°$ C., e.g. room temperature, is preferred.

The starting pyridinecarbonyl compounds of formula II and the thiobenzoic acid hydrazides of formula III are known and can be obtained by processes analogous to known ones. The substituted 2,3-diazabutadienes of formula IV, which as novel compounds likewise constitute an object of the present invention, can be obtained by procedures analogous to known ones (q.v. W. T. Flowers et al., J. Chem. Soc., Perkin. Trans., 1 (2), p. 349, 1981) as follows:

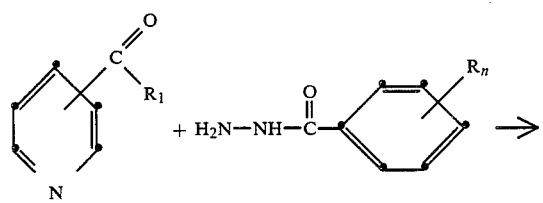

-continued

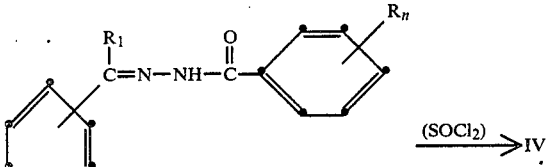

in which formulae $R_1$, R and n are as defined above.

It has been found that the compounds of formulae I and Ia exhibit excellent activity as pesticides, while being well tolerated by plants and having low mammalian toxicity to warm-blooded animals. The compounds of formulae I and Ia are suitable in particular for controlling pests that attack plants and animals.

In particular, the compounds of formulae I and Ia are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of the invention corresponds to a mortality of at least 50–60% of the above pests.

Most particularly plant-destructive insects, especially plant-destructive insects in ornamentals and crops of useful plants, in particular in cotton, vegetable, rice and fruit crops, can be controlled with the compounds of formulae I and Ia. In this connection, particular attention is drawn to the fact that the compounds of formulae I and Ia have both a strongly pronounced systemic and, in particular, contact action against sucking insects, especially against sucking insects of the Aphididae family (e.g. against Aphis fabae, Aphis craccivora and Myzus persicae), which can only be controlled with difficulty using known pesticides.

The compounds of formulae I and Ia also exhibit a good activity against larval insect stages and nymphs, especially of noxious feeding insects. In particular, the compounds of formulae I and Ia can be used with great success against plant-destructive cicadas, especially in rice crops. The compounds of formulae I and Ia are also suitable for controlling ectoparasites, e.g. Lucilia sericata, and ticks on domestic animals and productive livestock, e.g. by treating animals, barns, stables etc., and pastures.

The activity of the compounds of formulae I and Ia and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formulae I and Ia are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or Ia or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I or Ia to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions of this invention usually contain—based on the weight—0.1 to 99%, preferably 0.1 to 95%, of a compound of formula I or Ia or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1

Preparation of 2-(4-chlorophenyl)-5-(pyrid-3-yl)-4,5-dihydro-1,3,4-thiadiazole 39.2 g of p-chlorothiobenzoic acid hydrazide are dissolved in 350 ml of ethanol. Under nitrogen, 21.4 g of pyridine-3-aldehyde (dissolved in 20 ml of ethanol) are added dropwise to this solution. The reaction temperature is kept at 20° C. by cooling. When the addition is complete, the reaction mixture is stirred for 1 hour at reflux temperature and subsequently filtered through finely particulate diatomaceous earth. The filtrate is concentrated to three quarters of its initial volume and the precipitated product is isolated by filtration, washed with hexane and dried, affording the title compound of the formula

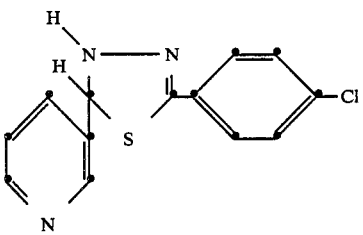

with a melting point of 106°–108° C. (compound 1.1).

EXAMPLE 2

Preparation of 2-(3-nitrophenyl)-5-(pyrid-3-yl)-4,5-dihydro-1,3,5-thiadiazole

A solution of 8.7 g of potassium hydroxide in 100 ml of ethanol is saturated with hydrogen sulfide. 8.7 g of potassium hydroxide in 100 ml of ethanol are added dropwise to this solution. With ice cooling, 22.4 g of 1-chloro-1-(3-nitrophenyl)-4-(3-pyridyl)-2,3-diazabutadiene are added in portions to the resultant solution. The reaction mixture is stirred for 1 hour at room temperature and then concentrated, and the residue is taken up in ethyl acetate. The ethyl acetate solution is washed twice with water and twice with saturated sodium chloride solution, dried over sodium sulfate and filtered, and the filtrate is concentrated by evaporation, thus affording the title compound of the formula

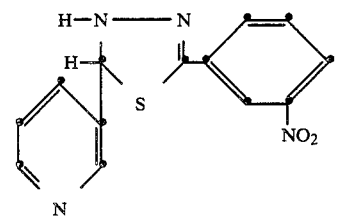

with a melting point of 109°–111° C. (compound 1.2).

The following compounds of formula Ia are prepared in accordance with the procedures described above:

| Compound | Position of pyridyl group | R₁ | R₂ | R₃ | Physical data |
|---|---|---|---|---|---|
| 1.3 | 2 | H | 4-Cl | H | m.p. 91–93° C. |
| 1.4 | 4 | H | 4-Cl | H | m.p. 145–147° C. |
| 1.5 | 3 | —CH₃ | 4-Cl | H | m.p. 119–120° C. |
| 1.6 | 3 | H | H | H | m.p. 70–73° C. |
| 1.7 | 3 | —CH₃ | H | H | $n_D^{20} = 1.6450$ |
| 1.8 | 4 | —CH₃ | 4-Cl | H | m.p. 123–125° C. |
| 1.9 | 2 | —CH₃ | 4-Cl | H | m.p. 92–93° C. |
| 1.10 | 3 | H | 2-Cl | H | m.p. 125–126° C. |
| 1.11 | 3 | H | 2-F | H | m.p. 78–80° C. |
| 1.12 | 3 | H | 4-CH₃ | H | m.p. 118–119° C. |
| 1.13 | 3 | H | 4-CF₃ | H | m.p. 98–100° C. |
| 1.14 | 3 | H | 3-F | H | m.p. 73–75° C. |
| 1.15 | 3 | H | 4-F | H | m.p. 103–105° C. |
| 1.16 | 3 | H | 4-Br | H | m.p. 126–128° C. |
| 1.17 | 3 | H | 3-Cl | H | m.p. 86–87° C. |
| 1.18 | 3 | H | 3-CH₃ | H | m.p. 80–82° C. |
| 1.19 | 3 | H | 4-OCH₃ | H | m.p. 93–94° C. |
| 1.20 | 3 | H | 3-Cl | 4-Cl | m.p. 104–108° C. |

The following compounds of formula Ia can also be obtained as described above:

| Position of pyridyl group | R₁ | R₂ | R₃ |
|---|---|---|---|
| 2 | n-C₄H₉ | H | H—CH₃ |
| 4 | H | H | 4-n-C₄H₉ |
| 2 | —CH₃ | 4-OCH₃ | H |
| 4 | —C₂H₅ | H | —OCH₃ |
| 2 | —n-C₃H₇ | 2-F | H |
| 4 | H | 2-Cl | 6-Cl |
| 3 | H | 2-Cl | 4-Cl |
| 3 | H | 2-Cl | 3-Cl |
| 3 | H | 3-F | 5-F |
| 3 | H | 3-F | 4-F |
| 3 | H | 2-F | 4-F |
| 3 | H | 2-F | 3-F |
| 3 | H | 4-OCF₃ | H |
| 3 | H | 4-OCF₂CHFCF₃ | H |
| 3 | H | 4-OCHF₂ | H |
| 3 | H | 4-CN | H |
| 3 | H | 4-O—phenyl | H |
| 3 | H | 4-CH₂—phenyl | H |
| 3 | H | 4-S—phenyl | H |
| 3 | H | 3-O—phenyl | H |
| 3 | H | 4-O—(3,5-Cl₂—pyridyl) | H |
| 3 | H | 4-C₂H₅ | H |
| 3 | H | 3-Cl | 5-Cl |

In addition, the following compounds corresponding to formula I can be obtained as described above:

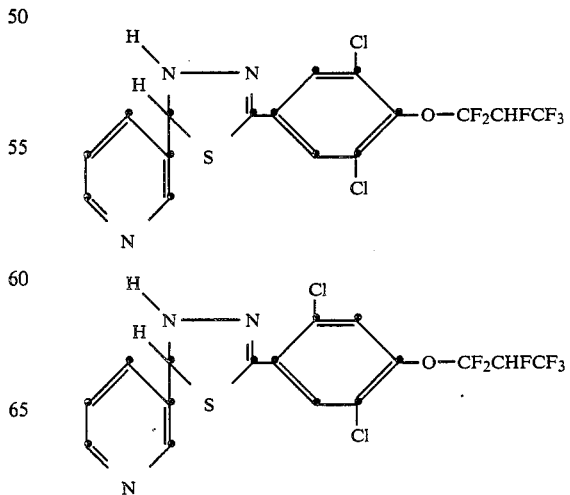

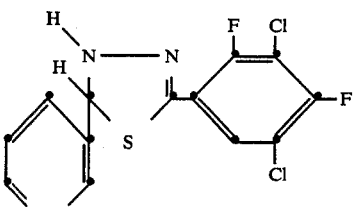

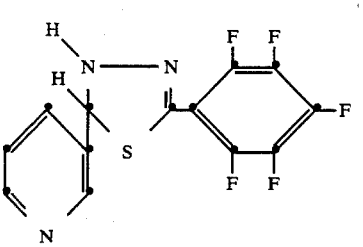

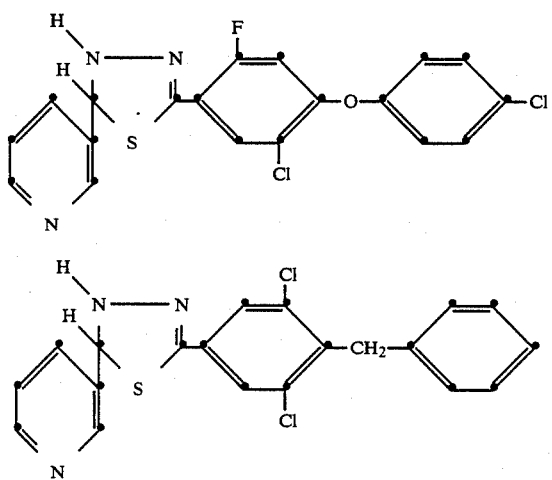

The following salts of a compound of formula Ia can also be obtained as described above:

| Compound | Position of pyridyl group | R₁ | R₂ | R₃ | Salt-forming acid | Physical data [°C.] |
|---|---|---|---|---|---|---|
| 2.1 | 3 | H | 4-Cl | H | oxalic acid | m.p. 200–201 |
| 2.2 | 3 | H | 4-Cl | H | HBr | m.p. 232–234 |
| 2.3 | 3 | H | 4-Cl | H | p-toluenesulfonic acid | m.p. 261–262 |
| 2.4 | 3 | H | 4-Cl | H | benzoic acid | m.p. 70–72 |
| 2.5 | 3 | H | 4-Cl | H | HCl | m.p. 192–193 |
| 2.6 | 3 | H | 4-Cl | H | HBr | m.p. 228–229 |

EXAMPLE 3

Formulations for active ingredients of formulae I and Ia according to Examples 1 and 2 or combinations thereof with other insecticides or acaricides (throughout, percentages are by weight)

| 1. Wettable powders | a | b | c |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with water to give suspensions of any desired concentration.

| 2. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | a | b |
|---|---|---|
| active ingredient or active ingredient combination | 5% | 8% |
| talcum | 95% | — |
| kaolin | — | 92% |

Ready for use dusts are obtained by mixing the active ingredient or active ingredient combination with the carrier, and grinding the mixture in a suitable mill.

| 4. Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| 5. Coated granulate | |
|---|---|
| active ingredient or active ingredient combination | 3% |
| polyethylene glycol (mol. wt. 200) | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 6. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |

-continued

| 6. Suspension concentrate | |
|---|---|
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

EXAMPLE 4

Active against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of Musca domestica are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formulae I and Ia according to Examples 1 and 2 exhibit good activity in this test.

EXAMPLE 5

Action against *Lucilia sericata (larvae)*

1 ml of an aqueous formulation containing 0.5% of test compound is added at 50° C. to 9 ml of a culture medium. Then about 30 freshly hatched Lucilia sericata larvae are added to the culture medium, and the insecticidal action is determined after 48 and 96 hours by evaluating the mortality rate.

In this test, compounds of formulae I and Ia according to Examples 1 and 2 exhibit good activity against Lucilia sericata.

EXAMPLE 6

Action against *Aëdes aegypti* (larvae)

A concentration of 200 ppm is obtained by pipetting a specific amount of a 0.1% solution of the test compound in acetone onto the surface of 150 ml of water in a beaker. After the acetone has evaporated, 30 to 40 two-day old larvae of *Aëdes des aegypti* are put into the beaker containing the test compound. Mortality counts are made after 2 and 7 days.

Compounds of formulae I and Ia according to Examples 1 and 2 exhibit good activity in this test.

EXAMPLE 7

Contact action against *Aphis craccivora*

Before the start of the test, 4- to 5-day old bean plants (*Vicia faba*) reared in pots are each populated with about 200 insects of the species *Aphis craccivora*. The treated plants are sprayed direct to drip point 24 hours later with an aqueous formulation containing the test compound. Two plants are used for each test compound at its given concentration. A mortality count is made after 24 and 72 hours respectively. The test is carried out at 21°–22° C. and at a relative humidity of about 55%.

In the test, compound 1.1 according to Example 1 effects 80 to 100% kill at 3 ppm. Compounds 1.6, 1.11, 2.1, 2.2, 2.3, 2.4 and 2.5 exhibit the same activity at 400 ppm.

EXAMPLE 8

Systemic action against *Aphis craccivora*

Bean plants which have grown roots are transplanted into pots containing 600 ccm of soil. Then 50 ml of a formulation (prepared from a 25% wettable powder) of the test compound in a concentration of 800 ppm are poured direct onto the soil in the pots.

After 24 hours the parts of the plants above the soil are populated with aphids of the species *Aphis craccivora* and a plastic cylinder is then slipped over the plants to protect the aphids from any possible contact with the test substance either directly or via the gas phase.

A mortality count is made 48 and 72 hours respectively after the start of the test. Two plants, each in a separte pot, are used for each test substance at its given concentration. The test is carried out at 25° C. and about 70% relative humidity.

Compounds of formulae I and Ia according to Examples 1 and 2 exhibit good activity in this test.

EXAMPLE 9

Contact action against *Myzus persicae*

4- to 5-day old bean plants (*Vicia faba*) which have been reared in water are each populated with about 200 aphids of the species *Myzus persicae* before the start of the test. The treated plants are sprayed direct to drip point 24 hours later with an aqueous suspension containing the test compound in a concentration of up to 200 ppm. Two plants are used for each compound at its given concentration. An evaluation of percentage morcidal tality is made 24 and 72 hours respectively after application. The test is carried out at 20°–22° C. and about 60% relative humidity.

In this test, 80 to 100% kill is effected by compound 1.1 according to Example 1 at 200 ppm, by compound 2.5 at 3 ppm and by compounds 2.1, 2.2, 2.3 and 2.4 at 50 ppm.

EXAMPLE 10

Systemic action against *Myzus persicae*

Cabbage plants which have grown roots are transplanted in the 4- to 5-leaf stage into pots containing 60 ccm of soil. Then 50 ml of an aqueous formulation (prepared from a 25% wettable powder) of the test compound in a concentration of 800 ppm are poured direct onto the soil.

After 24 hours the parts of the plants above the soil are populated with aphids of the species *Myzus persicae* and plastic cylinders are then slipped over the plants to protect the aphids from any possible contact with the test substance either directly or via the gas phase.

The evaluation of percentage mortality is made 48 hours after the start of the test. Two plants, each in a separate pot, are used for each test substance at its given concentration. The test is carried out at about 25° C. and 60% relative humidity.

Compounds of formulae I and Ia according to Examples 1 and 2 exhibit good activity in this test.

EXAMPLE 11

Lead penetration action against *Aphis craccivora*

A small shoot of *Vicia faba*, which is highly infested with aphids of the species *Aphis craccivora*, is placed in each of a number of 8 cm high plastic beakers (diameter about 6 cm). Each beaker is covered with a plastic lid having a punched opening of 2 cm diameter in the centre. A leaf of a *Vicia faba*-plant is then placed over the opening in the lid without separating this leaf from the potted plant. The leaf is then fixed on the beaker with a second punched lid above the opening of the first lid. From underneath, i.e. through the opening of the first lid, the aphids in the beaker then infect the leaf of the plant used as bait. An aqueous formulation of the test compound is then applied in a concentration of 400 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds of formulae I and Ia according to Examples 1 and 2 exhibit good activity in this test.

EXAMPLE 12

Stomach poison action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 800 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

Compounds of formulae I and Ia according to Examples 1 and 2 exhibit good activity in this test.

EXAMPLE 13

Ovicidal action against *Laodelphax striatellus* and *Nilaparvata lugens*

The test ist carried out with growing plants. For this purpose 4 rice plants (thickness of stem 8 mm; height about 20 cm) are planted into each of a number of pots (diameter 8 cm).

The plants in each pot are sprayed on a rotary table with 100 ml of an acetonic solution containing 400 ppm of the respective test compound. After the spray coating has dried, each plant is populated with 3 adult females. To prevent the females from escaping, a glass cylinder is slipped over each of the plants and sealed with a gauze top. The females are left on the treated plant for 4 days for oviposition and are then removed.

About 8 days after the females have been placed on the plants, the young cicadas hatch from the eggs and a count is made. The percentage mortality is calculated by comparing the number of larvae which have hatched on the treated plants with the number which have hatched on the untreated control plants.

Compounds of formulae I and Ia according to Examples I and 2 exhibit good ovicidal activity in this test.

What is claimed is:

1. A compound of formula I

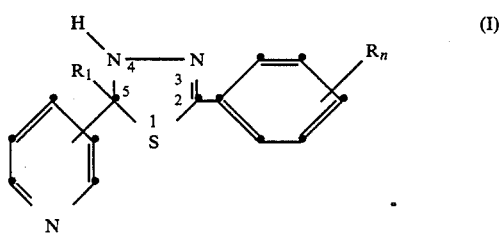

wherein $R_1$ is hydrogen or $C_1$–$C_4$alkyl;

R is hydrogen, $C_1$–$C_4$alkyl, halogen, nitro, cyano, $C_1$–$C_4$alkoxy, $C_1$–$C_4$alkylthio, $C_1$–$C_4$haloalkyl containing 1 to 9 halogen atoms, $C_1$–$C_4$haloalkylthio containing 1 to 9 halogen atoms, $C_1$–$C_4$haloalkylthio containing 1 to 9 halogen atoms, phenyl, phenylalkyl, phenoxy, phenylthio, pyridyloxy or phenyl, phenylalkyl, phenoxy, phenylthio or pyridyloxy, which is substituted by one to three substituents selected from $C_1$–$C_4$alkyl, halogen, nitro, cyano, $C_1$–$C_4$alkoxy, $C_1$–$C_4$alkylthio, $C_1$–$C_4$haloalkyl containing 1 to 9 halogen atoms, $C_1$–$C_4$haloalkoxy containing 1 to 9 halogen atoms and $C_1$–$C_4$haloalkylthio containing 1 to 9 halogen atoms and n is a value from 1 to 5;

or a salt or optical isomer thereof.

2. A compound of formula I according to claim 1, wherein $R_1$ is hydrogen or $C_1$–$C_4$alkyl;

R is hydrogen, $C_1$–$C_4$alkyl, halogen, nitro, cyano, $C_1$–$C_4$alkoxy, $C_1$–$C_4$alkylthio, $C_1$–$C_4$haloalkyl containing 1 to 9 halogen atoms, $C_1$–$C_4$haloalkoxy containing 1 to 9 halogen atoms or $C_1$–$C_4$haloalkylthio containing 1 to 9 halogen atoms and n is a value from 1 to 5;

or a salt or optical isomer thereof.

3. A compound according to claim 1, wherein n is 1 or 2.

4. A compound according to claim 3 of formula Ia

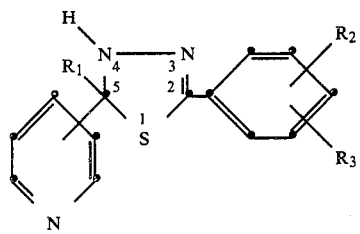

wherein
- $R_1$ is hydrogen or $C_1$–$C_4$alkyl;
- $R_2$ and $R_3$ are each independently of the other hydrogen, halogen, $C_1$–$C_4$alkyl, trifluoromethyl, $C_1$–$C_4$alkoxy or nitro;
- or a salt thereof.

5. A compound of formula Ia according to claim 4, wherein
- $R_1$ is hydrogen, methyl or ethyl;
- $R_2$ and $R_3$ are each independently of the other hydrogen or halogen which is in the 2- and/or 4-position.

6. A compound of formula Ia according to claim 4, wherein $R_3$ is hydrogen.

7. A compound according to claim 1, wherein $R_1$ is hydrogen.

8. A compound according to one of the claims 1 or 4, wherein in formula I or Ia the pyridyl group is attached in its 3-position to the 4,5-dihydro-1,3,4-thiadiazole ring in the 5-position.

9. A compound according to claim 6 of formula

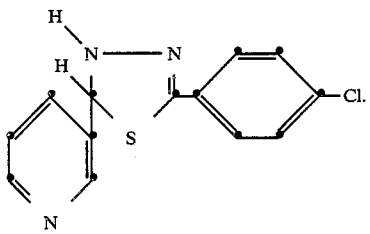

10. A compound according to claim 6 of formula

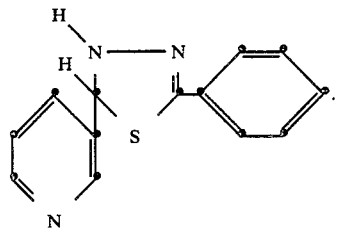

11. A compound according to claim 6 of formula

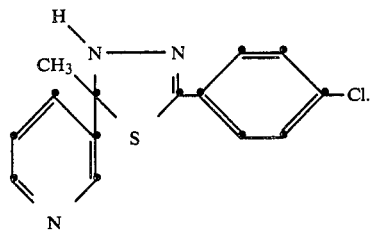

12. An insecticidal and acaricidal composition which contains as active ingredient an insecticidally and acaricidally effective amount of a compound according to claim 1, together with a suitable carrier and/or other adjuvant.

13. A method for controlling pests selected from insects and representatives of the order Acarina, which method comprises contacting or treating said pests or their various development stages and/or the locus thereof with a pesticidally effective amount of a compound of formula I according to claim 1 or with a composition containing a pesticidally effective amount of such a compound, together with a suitable carrier and/or other adjuvant.

14. A method according to claim 13 for controlling insects and representatives of the order Acarina on animals and plants.

15. A method according to claim 14 for controlling plant-destructive insects.

16. A method according to claim 15 for controlling plant-destructive sucking insects.

* * * * *